United States Patent [19]

Mazour et al.

[11] 4,032,602
[45] June 28, 1977

[54] PROCESS FOR THE PRODUCTION OF PHOSPHITE CHLORIDES

[75] Inventors: Zdenek Mazour, Frenkendorf; Heimo Brunetti, Reinach, both of Switzerland

[73] Assignee: Ciba-Geigy Corporation, Ardsley, N.Y.

[22] Filed: Sept. 29, 1975

[21] Appl. No.: 617,779

[52] U.S. Cl. .............................. 260/972; 260/960
[51] Int. Cl.² .......................................... C07F 9/20
[58] Field of Search ........................... 260/960, 972

[56] References Cited
OTHER PUBLICATIONS

Cook et al., "J. Chem. Soci.," (London), (1949), IV, pp. 2921–2927.

Primary Examiner—Anton H. Sutto
Attorney, Agent, or Firm—Karl F. Jorda

[57] ABSTRACT

Process for the production of phosphite chlorides comprising the reaction of phosphorus trichloride and a trialkyl phosphite or a triphenyl phosphite in the presence of a hydrous quaternary compound of nitrogen or phosphorus.

10 Claims, No Drawings

PROCESS FOR THE PRODUCTION OF PHOSPHITE CHLORIDES

The present invention relates to a process for the production of phosphite chlorides of the formula I

wherein
R represents $C_1$–$C_{18}$-alkyl or optionally substituted phenyl, and
R′ represents OR or chlorine by reaction of phosphorus trichloride with a symmetrical trialkyl- or triphenylphosphite that is present in the amount necessary for the formation of the phosphite chlorides or phosphite dichlorides.

Preferred among the compounds of the formula I are those in which R represents $C_1$–$C_5$-alkyl. The radical R as a phenyl group can be mono- to tri-substituted by $C_1$–$C_{18}$-alkyl, $C_1$–$C_{18}$-alkoxy or halogen, especially by chlorine or bromine, with the total number of carbon atoms for more than one alkyl or alkoxy group not being greater than 18.

The phosphite chlorides of the formula I obtainable by the process according to the invention, particularly those compounds in which R represents an alkyl group having 1 to 5 carbon atoms and R′ represents chlorine or an alkoxy group having 1 to 5 carbon atoms, are valuable intermediates for the production of O,S-dialkylthiosphosphates of the type described in the U.S. Pat. applications Ser. No. 558,589, filed on Mar. 14, 1975, 377,855, filed on July 9, 1973, Ser. No. 394,694, filed on Sept. 6, 1973, Ser. No. 489,281, filed on July 17, 1974 and Ser. No. 408,874, filed on Oct. 23, 1973. By virtue of their excellent insecticidal action, these compounds can be used as pest-control agents.

The O,S-dialkylthiophosphates of the type described in the aforementioned patent applications are produced, for example, by reacting a dialkylchlorophosphite of the formula I with an alkylsulphenyl chloride to give the corresponding O,S-dialkylthiophosphoric acid chloride, which yields, by further reaction with a phenolate or enolate, the desired final product (see J. Org. Chem. 30, 3218, (1965)).

With the use of a variant of this process, the O,S-dialkylthiophosphates of the type described in the aforementioned applications can be produced by firstly reacting an alkylphosphite dichloride of the formula I with an alkylsulphenyl chloride to the corresponding S-alkylthiophosphoric acid dichloride, and replacing in this the two chloride atoms successively by an alkoxy group and a phenoxy group.

The phosphite chlorides of the formula I can moreover be used as intermediates for the production of phosphites containing various alkyl groups or alkyl and phenyl groups in the molecule. Such mixed phosphites can be used for the stabilisation of epoxy compounds, and together with cadmium benzoate or cerium benzoate for the colour stabilisation of difficulty combustible polycarbonates (see U.S. Pat. No. 3,769,367 and British patent specification No. 1,180,836, which is based on the U.S. patent application Ser. No. 539,652, filed on Apr. 4, 1966).

A known process for the production of the dialkylphosphite chlorides and alkylphosphite dichlorides required as starting materials in the aforementioned processes for the production of O,S-dialkylthiophosphoric acid esters comprises reacting phosphorous trichloride in the presence of an acid acceptor, e.g. N,N-dimethylaniline or N,N-diethylaniline, with an alkanol (see H. G. Cook et al., J. Chem. Soc. 1949, Part IV, pp. 2921–2927, and A. J. Razumov et al., Chem. Abstr. 60, 157lg–h (1964). With this process the phosphite chlorides of the formula I are obtained merely in yields of 20 – 35% of theory. The processing of the reaction mixtures obtained is rendered difficult in that phosphine is formed as by-product, which constitutes a safety risk by virtue of its spontaneous inflammability. This process is therefore unsuitable for a production of phosphite chlorides on a commercial scale.

A variation of this process is described by J. Michalski et al., J. Chem. Soc. 1961, 4904, which comprises the use of a pyridine/diethylaniline mixture as an acid acceptor. Although higher yields can be obtained by this process, it is technically unsatisfactory on account of the necessary complicated working up of a mixture of hydrochlorides of two different bases.

It has also already been suggested that phosphite chlorides of the formula I be produced by reaction of trialkylphosphites with o-dihydroxybenzenephosphoric acid trichloride (see J. Gloede et al., J. Prakt. Chem. 316, 703–704, (1974)). Although it is possible by this process to obtain the phosphite chlorides of the formula I in a yields of 81% of theory, this process too is unsuitable for production of phosphite chlorides on a commercial scale since the o-dihydroxybenzenephosphoric acid trichloride required as starting material is on the one hand too expensive and on the other hand not available in large quantities. Furthermore, the process is rendered additionally costly as a result of the laborious processing of the cyclic o-dihydroxybenzenephosphate occurring in the reaction.

It is further known how to produce phosphite chlorides of the formula I by reaction of phosphorus trichloride with symmetrical trialkylphosphites (see J. Chem. Soc. 1949, IV, 2921–2927). There has thus been obtained for example, by refluxing for half an hour a mixture of triethylphosphite and phosphorus trichloride, diethylchlorophosphite in a yield of 44% of theory. In addition there were formed a small amount of higher-boiling products and a solid residue. In view of the low yield and the ecologically problematic by-products, this process too is unsuitable for the commercial production of alkylphosphite chlorides.

It has now been found that the phosphite chlorides of the formula I can be produced, in a short time and in yields appreciably higher than those hitherto obtained, by reaction of phosphorus trichloride with a symmetrical trialkylphosphite or triphenylphosphite that is present in the amount necessary for the formation of the phosphite chlorides or phosphite dichlorides if the said reaction of phosphorus trichloride with the symmetrical trialkyl phosphite or triphenylphosphite is performed in the presence of a hydrous quaternary compound of nitrogen or of phosphorus at a temperature of between −15° C and +75° C. Quaternary compounds of nitrogen that are suitable according to the invention are, in particular, those of the formula II

wherein
R$_1$ represents C$_1$–C$_{18}$-alkyl, C$_7$–C$_9$-phenylalkyl or C$_6$–C$_{10}$-aryl,
R$_2$ represents C$_1$–C$_1$-alkyl or C$_7$–C$_9$-phenylalkyl,
R$_3$ represents C$_1$–C$_{12}$-alkyl or C$_7$–C$_9$-phenylalkyl,
R$_4$ represents C$_1$–C$_4$-alkyl, and
X represents chlorine or bromine, whereby the radicals R$_1$ and R$_2$ together can also represent a pentamethylene group.

Preferred among the quaternary nitrogen compounds of the above formula II are those wherein R$_1$ represents C$_1$–C$_4$-alkyl, benzyl or phenyl, R$_2$ represents C$_1$–C$_4$-alkyl or benzyl, R$_3$ represents C$_1$–$_{C4}$-alkyl or benzyl, and R$_4$ represents C$_1$–$_{C2}$-alkyl.

Suitable quaternary compounds of phosphorus are, in particular, those of the formula III

wherein
R$_5$ represents C$_1$–C$_{18}$-alkyl or phenyl,
R$_6$, R$_7$ and R$_8$ each independently represent C$_1$-C$_8$-alkyl or phenyl, and
X represents chlorine or bromine.

Preferred compounds among the quaternary phosphorus compounds of the above formula III are those wherein R$_5$ represents phenyl, and R$_6$, R$_7$ and R$_8$ each independently represent phenyl or C$_1$–C$_4$-alkyl.

The water content of the aforementioned quaternary compounds of nitrogen and phosphorus is according to the invention between 1 and 15 MOl-%, preferably between 3 and 9 Mol-%. The amount of quaternary compound that is added to the reaction mixture is preferably between 1 and 10 Mol-%, relative to the total molar number. The use of appreciably greater amounts of quaternary compound is likewise possible but not necessary.

Suitable quaternary compounds of nitrogen and of phosphorus are according to the invention, in particular, quaternary ammonium salts and quaternary phosphonium salts, e.g. tetramethylammonium chloride, tetraethylammonium chloride, benzyltrimethylammonium chloride, benzyltriethylammonium chloride and ethyltriphenylphosphonium bromide, all having a water content of 1 to 15 Mol-%. Tetraethylammonium chloride and benzyltriethylammonium chloride having a water content of 3 to 9 Mol-% are particularly suitable.

Within the given temperature range of −15° C to +75° C, in which the reaction can be carried out, the preferred range is between −5° C and 40° C, especially between 0° C and 25° C.

The reaction is performed according to the invention by a process in which one of the two reactants is brought together with the quaternary compound and the second reactant is then added. The reaction can be performed in the presence of an inert solvent, for example in the presence of an aliphatic or aromatic hydrocarbon or of an ether such as hexane, cyclohexane, benzene, toluene, chlorobenzene, diethyl ether, tetrahydrofuran or dioxane. Preferably, however, it is preformed in the absence of a solvent. The reaction times are between a few minutes and 24 hours, preferably between 30 minutes and 10 hours. It is important to thoroughly mix the reaction mixture during the reaction. After completion of the reaction, the quaternary compound is filtered off. The catalyst-free reaction mixture thus obtained contains the formed phosphite chloride of the formula I in good yield. It can be further reacted in its existing form, or the formed phosphite chloride of the formula can for further purification be separated by distillation from the reaction mixture. It is advantageous to perform the distillation-separation of the phosphite chloride of the formula I at as low a temperature as possible. Provided that they are not immediately further processed, the phosphite chlorides of the formula I produced according to the invention can be stored with cooling for a prolonged period of time.

In the case of a further simplification of the process of the invention, the arrangement can be that phosphorus trichloride is reacted with a compound of the formula ROH in the presence of a stoichiometric amount of a nitrogen base, such as triethylamine of pyridine, and one of the inert solvents to give trialkyl- or triphenylphosphite, the appropriate amount of quaternary compound is added and an addition is then made dropwise of the phosphorus trichloride. After separation of the precipitated amine hydrochlorides, further processing is then carried out as described above.

By carrying out according to the invention the reaction of symmetrical trialkyl- or triphenylphosphites and phosphorus trichloride in the presence of quaternary ammonium salts or hosphonium salts the result achieved is that the equilibrium between symmetrical trialkyl- or triphenylphosphite on the one hand and phosphorus trichloride on the other hand is established rapidly and under mild conditions, It is thus for example possible, especially when the reaction is performed at a temperature exceeding 60° C, to process by distillation the reaction mixture, after addition of the second constituent, after only a few minutes. By virtue of these short reaction times at a temperature of over 60° C, the formation of undesired by-products, e.g. the formation of spontaneously inflammable phosphines such as readily occur with longer retention times at temperatures of above 60° C, is avoided. At the same time, the yield of the desired final product compared with the yield obtained by known processes is greatly increased. The process of the invention thus renders possible for the first time the nonproblematic large-scale production of phosphite chlorides of the formula I; moreover, the said production process can be carried out also as a continuous process. Furthermore, the phosphite chlorides of the formula I can be produced in a particularly pure form by the process of the invention. A further advantage of the process according to the invention is that the filtered-off catalyst can be used again after addition of the appropriate amount of water.

The process of the invention is further illustrated by the following Examples.

EXAMPLE 1

Dimethylchlorophosphite 32.5 g (0.24 mole) of phosphorus trichloride is added dropwise at 0° to 5° C, with stirring, to a mixture of 62.04 g (0.5 mole) of trimethylphosphite and 10.0 g of tetraethylammonium chloride (water content 7%). After completion of the addition, the reaction mixture is heated to room temperature and stirred for a further 24 hours at this temperature. The tetraethylammonium chloride is subsequently filtered off, and the formed dimethylchlorophosphite is isolated by distillation of the filtrate under reduced pressure. There is obtained 65.0 g (71% of theory, relative to phosphorus trichloride) of dimethylchlorophosphite, b.p. 29°–31° C/35 Torr.

EXAMPLE 2

Ethyldichlorophosphite 137.0 g (1.0 mole) of phosphorus trichloride is slowly added dropwise at 45°–50° C, with stirring, to a mixture of 83.0 g (0.5 mole) of triethylphosphite and 15.0 g of benzyltriethylammonium chloride (water content of 6.8%). After completion of the addition, the reaction mixture is subsequently stirred for 16 hours at 50° C. The reaction mixture is afterwards cooled to 0°–5° C and the benzyltriethylammonium chloride is separated by filtration. The filtrate obtained consists to the extent of about 92–95% of ethyldichlorophosphite. The yield amounts to approx. 92–95% of theory. On vacuum distillation of the crude ethyldichlorophosphite there is obtained 187–198 g (85–90% of theory) of ethyldichlorophosphite, b.p. 47°–52° C/13 Torr. For the further reaction, it is of course possible in most cases to use the crude ethyldichlorophosphite.

EXAMPLE 3

Diethylchlorophosphite 65.0 g (0.475 mole) of phosphorus trichloride is slowly added dropwise at 5 to 10° C, with vigorous stirring, to a mixture of 166.0 g (1.0 mole) of triethylphosphite and 15.0 g of benzyltriethylammonium chloride (water content 7%). The reaction mixture is subsequently heated to room temperature and stirred for a further 6 hours at this temperature. The benzyltriethylammonium chloride is then filtered off, and the formed diethylchlorophosphite is isolated from the filtrate by distillation under reduced pressure. There is obtained 156.0 g (70% of theory, relative to phosphorus trichloride) of diethylchlorphosphite, b.p. 40° to 41° C/12 Torr.

EXAMPLE 4

Diethylchlorophosphite 65.0 g (0.475 mole) of phosphorus trichloride is slowly added dropwise at 5° to 10° C, with vigorous stirring, to a mixture of 166.0 g (1.0 mole) of triethylphosphite and 10.0 g of tetraethylammonium chloride (water content 9%). After completion of the addition, the reaction mixture is heated to room temperature and stirred at this temperature for a further 24 hours. The tetraethylammonium chloride is afterwards filtered off and the formed diethylchlorophosphite is isolated from the filtrate by distillation under reduced pressure. There is obtained 160.0 g (71.7% of theory, relative to phosphorus trichloride) of diethylchlorphosphite, b.p. 40° to 41° C/12 Torr.

EXAMPLE 5

Diethylchlorophosphite 65.0 g (0.475 mole) of phosphorus trichloride is added dropwise at 5° to 10° C, with vigorous stirring, to a mixture of 166.0 g (1.0 mole) of triethylphosphite and 10.0 g of ethyltriphenylphosphonium bromide (water content 8%). After completion of the addition, the reaction mixture is heated to room temperature and stirred for a further 24 hours at this temperature. The ethyltriphenylphosphonium bromide is afterwards filtered off and the formed diethylchlorophosphite is isolated from the filtrate by distillation under reduced pressure. There is obtained 145.0 g (65% of theory, relative to phosphorus trichloride) of diethylchlorophosphite, b.p. 40° to 41° C/12 Torr.

EXAMPLE 6

Di-n-butylchlorophosphite 17.0 g (0.125 mole) of phosphorus trichloride is added dropwise at 5° to 10° C, with vigorous stirring, to a mixture of 62.5 g (0.25 mole) of tri-n-butylphosphite and 5.0 g of benzyltriethylammonium chloride (water content 7%). After completion of the addition, the reaction mixture is heated to room temperature and stirred for a further 8 hours at this temperature. After separation of the benzyltriethylammonium chloride by filtration there is obtained, by distillation of the filtrate under reduced pressure, 51.8 g (65% of theory, relative to phosphorus trichloride) of di-n-butyl-chlorophosphite, b.p. 96° to 98° C/10 Torr.

EXAMPLE 7

Didecychlorophosphite 3.42 g (0.025 mole) of phosphorous trichloride is slowly added dropwise at 25° to 30° C, with vigorous stirring, to a mixture of 25.14 g (0.05 mole) of tridecylphosphite and 2.0 g of tetraethylammonium chloride (water content 8%). After completion of the addition, stirring is maintained for a further 5 hours at 25° to 30° C, and the tetraethylammonium chloride is then filtered off. There is obtained 27.5 g of crude didecylchlorophosphite in the form of a nondistillable viscous oil (yield = 96% of theory).

We claim:

1. A process for the production of phosphite chlorides of the formula I

wherein
  R represents $C_1$–$C_{18}$ alkyl, phenyl or phenyl mono-, di- or tri-substituted by $C_1$–$C_{18}$ alkyl, $C_1$–$C_{18}$ alkoxy or halogen with the total number of carbon atoms for more than one alkyl or alkoxy group not being greater than 18, and
  R' represents OR or chlorine, wherein R has the definition given above which comprises reacting phosphorus trichloride with a symmetrical trialkyl- or tri(substituted) phenyl phosphite that is present in the amount necessary for the formation of the phosphite chlorides of formula I at a temperature of between 15° C and 75° C and in the presence of a hydrous quaternary compound of nitrogen or of phosphorus, respectively, of the formula II

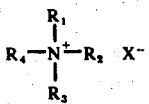

wherein
R₁ represents $C_1$–$C_{18}$-alkyl, $C_7$–$C_9$-phenylalkyl or $C_6$–$C_{10}$-aryl,
R₂ represents $C_1$–$C_1$-alkyl or $C_7$–$C_9$-phenylalkyl,
R₃ represents $C_1$–$C_{12}$-alkyl or $C_7$–$C_9$-phenylalkyl,
R₄ represents $C_1$–$C_4$-alkyl, and
X represents chlorine or bromine, whereby the radicals R₁ and R₂ together can also represent a pentamethylene group and of the formula III

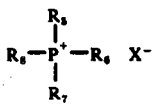

wherein
R₅ represents $C_1$–$C_{18}$ alkyl or phenyl,
R₆, R₇ and R₈ each independently represent $C_1$–$C_8$ alkyl or phenyl, and
X represents chlorine or bromine.

2. Process according to claim 1 wherein there is used a quaternary nitrogen compound of the formula II wherein R₁ represents $C_1$–$C_4$-alkyl, benzyl or phenyl, R₂ represents $C_1$–$C_4$-alkyl or benzyl, R₃ represents $C_1$–$C_4$-alkyl or benzyl, and R₄ represents $C_1$–$C_2$-alkyl.

3. Process according to claim 1 wherein there is used a quaternary phosphorus compound of the formula III wherein R₅ represents phenyl, and R₆, R₇ and R₈ each independently represent phenyl or $C_1$–$C_4$-alkyl.

4. Process according to claim 1 wherein there is used as quaternary compound of nitrogen a quaternary ammonium salt from the group tetramethylammonium chloride, tetraethylammonium chloride, benzyltrimethylammonium chloride and benzyltriethylammonium chloride, all having a water content of 1 to 15 percent by weight.

5. Process according to claim 1 wherein the quaternary compound of phosphorus used is ethyltriphenylphosphonium bromide having a water content of 1 to 15%.

6. Process according to claim 1 wherein the quaternary compound of nitrogen used is tetraethylammonium chloride having a water content of 3 to 9 percent by weight.

7. Process according to claim 1 wherein the quaternary compound of nitrogen used is benzyltriethylammonium chloride having a water content of 3 to 9 percent by weight.

8. Process according to claim 1 wherein the quaternary compound of the formula II is used in an amount of 1 to 10 Mol-%, relative to the total molar number of the starting products.

9. Process according to claim 1 wherein the reaction is performed at a temperature of between −5° C and 40° C.

10. Process according to claim 1 wherein the reaction is performed at a temperature of between 0° C and 25° C.

* * * * *

UNITED STATES PATENT AND TRADEMARK OFFICE
CERTIFICATE OF CORRECTION

PATENT NO. : 4,032,602
DATED : June 28, 1977
INVENTOR(S) : Zdenek Mazour and Heimo Brunetti It is certified that error appears in the above-identified patent and that said Letters Patent are hereby corrected as shown below:

Column 1, line 56 "chloride" should read -- chlorine --.

Column 3, line 10, "$R_2$ represents $C_1$-$C_1$-alkyl" should read -- $R_2$ represents $C_1$-$C_{18}$-alkyl --.

In the Claims, claim 1, column 7, line 10, "$R_2$ represents $C_1$-$C_1$-alkyl" should read -- $R_2$ represents $C_1$-$C_{18}$-alkyl --.

Signed and Sealed this

Twenty-seventh Day of September 1977

[SEAL]

Attest:

RUTH C. MASON
Attesting Officer

LUTRELLE F. PARKER
Acting Commissioner of Patents and Trademarks